US006881201B1

(12) United States Patent
Duchamp

(10) Patent No.: US 6,881,201 B1
(45) Date of Patent: Apr. 19, 2005

(54) BALLOON CATHETER HAVING A SPIRAL CUT DISTAL END

(75) Inventor: Jacky G. Duchamp, Campbell, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 128 days.

(21) Appl. No.: 10/322,209

(22) Filed: Dec. 18, 2002

(51) Int. Cl.[7] .............................................. A61M 29/00
(52) U.S. Cl. .................................................... 604/96.01
(58) Field of Search ........... 604/96.01, 101.01–101.05, 604/915–921, 103.01–103.09, 523, 524, 604/526, 527, 534; 606/191–194

(56) References Cited

U.S. PATENT DOCUMENTS

| | | | |
|---|---|---|---|
| 4,569,347 A | 2/1986 | Frisbie | |
| 4,636,346 A * | 1/1987 | Gold et al. | 264/139 |
| 4,921,983 A | 5/1990 | Siegmeier et al. | |
| 5,344,413 A | 9/1994 | Allman et al. | |
| 5,533,988 A * | 7/1996 | Dickerson et al. | 604/523 |
| 5,599,319 A | 2/1997 | Stevens | |
| 5,599,325 A * | 2/1997 | Ju et al. | 604/524 |
| 5,762,637 A | 6/1998 | Berg et al. | |
| 6,165,152 A | 12/2000 | Becker et al. | |
| 6,206,852 B1 | 3/2001 | Lee | |
| 6,368,301 B1 | 4/2002 | Hamilton et al. | |
| 6,403,011 B1 | 6/2002 | Stamberg | |
| 6,500,157 B1 * | 12/2002 | Luther | 604/264 |
| 6,575,934 B1 * | 6/2003 | Duchamp | 604/102.02 |

* cited by examiner

*Primary Examiner*—Manuel Mendez
(74) *Attorney, Agent, or Firm*—Fulwider Patton Lee & Utecht LLP

(57) ABSTRACT

A catheter having an elongated shaft, a balloon on a distal shaft section, and a distal tip having at least a section formed by a distal end portion of the shaft and an outer sheath member fused together. The outer sheath member has a sidewall break at least partially filled with the polymeric material of the outer surface of the distal end portion of the shaft. The outer sheath member preferably comprises a first polymeric material having a higher Shore durometer hardness than a second polymeric material forming the outer surface of the shaft distal end portion. One aspect of the invention is directed to a method of making a balloon catheter, in which the polymeric material of the outer surface of the shaft is caused to soften and flow into the opening formed by the break in the sidewall of the outer sheath, thus forming the distal tip.

15 Claims, 2 Drawing Sheets

BALLOON CATHETER HAVING A SPIRAL CUT DISTAL END

BACKGROUND OF THE INVENTION

This invention generally relates to catheters, and particularly intravascular catheters for use in percutaneous transluminal coronary angioplasty (PTCA) or for the delivery of stents.

In percutaneous transluminal coronary angioplasty (PTCA) procedures a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter and the guidewire can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter, and expanded within the patient's artery to a larger diameter by expansion of the balloon. The balloon is deflated to remove the catheter and the stent left in place within the artery at the site of the dilated lesion. See for example, U.S. Pat. No. 5,507,768 (Lau et al.) and U.S. Pat. No. 5,458,615 (Klemm et al.), which are incorporated herein by reference.

An essential step in effectively performing a PTCA procedure is properly positioning the balloon catheter at a desired location within the coronary artery. To properly position the balloon at the stenosed region, the catheter shaft must be able to transmit force along the length of the catheter shaft to allow it to be pushed through the vasculature. However, the catheter shaft must also retain sufficient flexibility to allow it to track over a guidewire through the often tortuous vasculature. Additionally, the catheter also must have good crossability (i.e., the ability of the catheter distal end to cross stenosed portions of the vascular anatomy).

Conventional intravascular catheters have commonly included a soft distal tip to prevent or minimize injury to the vessel during advancement of the catheter therein. One difficulty has been forming a connection between a soft tip member and the catheter which is sufficiently strong to prevent disengagement of the soft tip or kinking at the junction between the soft tip and catheter shaft. Additionally, it is necessary to balance the strength of the connection between the soft tip and the catheter shaft with the need to minimize the stiffness of the distal end of the catheter. Minimizing the stiffness of the distal end of the catheter results in improved maneuverability of the catheter.

Accordingly, it would be a significant advance to provide a catheter with a soft tip having improved performance. This invention satisfies these and other needs.

SUMMARY OF THE INVENTION

The invention is directed to a catheter having an elongated shaft, a balloon on a distal shaft section, and a distal tip having at least a section formed by a distal end portion of the shaft and an outer sheath member fused together. The outer sheath member has a sidewall break (e.g., a cut) at least partially filled with the polymeric material of the distal end portion of the shaft. The outer sheath member preferably comprises a first polymeric material having a higher Shore durometer hardness than a second polymeric material forming the outer surface of the shaft distal end portion. One aspect of the invention is directed to a method of making a balloon catheter, in which the distal end portion of the shaft is placed within the lumen of the outer sheath member and heat fusion bonded thereto, so that the polymeric material of the outer surface of the shaft is caused to soften and flow into the opening formed by the break in the sidewall of the outer sheath, thus forming the distal tip.

The sidewall break is preferably formed by mechanically cutting through the outer sheath member, although a variety of methods may alternatively be used to form the sidewall break including laser cutting. Thus, in one presently preferred embodiment, the sidewall break is formed by cutting a slit in the wall without removing polymeric material from the outer sheath. The break preferably extends through the sidewall from an outer to an inner surface of the outer sheath, thus allowing the polymeric material of the underlying section of the catheter to flow into the break during bonding the two together. As a result, the distal tip has distally increasing softness and flexibility, yet with high tensile and accordion strength.

In a presently preferred embodiment, the sidewall break spirals longitudinally at an angle relative to a longitudinal axis of the distal tip. The angle of the spiral preferably ranges from about 30 degrees to about 85 degrees, and in one embodiment ranges from about 30 to about 60 degrees, relative to the tip longitudinal axis. In one embodiment, the angle of the spiraling sidewall break varies along the length of the distal tip. For example, in one embodiment, the angle increases towards a distal end of the distal tip so that the space between the adjacent turns of the spiraling break decreases distally. Consequently, the distal tip has a distally increasing amount of polymeric material from the underlying section of the shaft interspersed in the wall of the outer sheath member, which results in increasingly higher flexibility toward the distal end of the distal tip. Specifically, in one embodiment, the bonding of the outer sheath member to the shaft to form the distal tip causes the flexibility of the outer sheath member to transform from a substantially uniform flexibility along its length to a distally increasing flexibility, due to the spreading out of the polymeric material of the outer sheath member with increasing amounts of shaft material per unit length of the outer sheath member. The angle of the spiraling sidewall break at the proximal end of the distal tip is typically about 30 to about 60 degrees, more specifically about 30 to about 45 degrees, and increases to a maximum angle toward the distal end of the distal tip of about 45 to about 85 degrees, more specifically about 45 to about 60 degrees. Although discussed below primarily in terms of the embodiment having a longitudinally spiraling sidewall break, the sidewall break may have alternative configurations, including discontinuous bands which may extend only partially around the circumference of the outer sheath member.

A balloon catheter of the invention generally comprises an elongated shaft having a proximal shaft section, a distal shaft section, an inflation lumen extending within the proximal and distal shaft sections, and a guidewire receiving lumen extending at least within the distal shaft section, and an inflatable balloon on the distal shaft section with an interior in fluid communication with the inflation lumen. The balloon typically has a proximal skirt section and a distal skirt section sealingly secured to the shaft, and an inflatable section therebetween. In a presently preferred embodiment, the shaft comprises an outer tubular member defining the inflation lumen, and an inner tubular member defining at least a portion of the guidewire receiving lumen. However, a variety of suitable shaft designs may be used including dual-lumen type shafts. The balloon catheter of the invention may comprise a variety of suitable balloon catheters, including coronary and peripheral dilatation catheters, stent delivery catheters, drug delivery catheters, and the like.

In one embodiment, the distal skirt section of the balloon forms the outer sheath member around the distal end of the shaft. In an alternative embodiment, the outer sheath member is a sleeve member having at least a portion located distal to the distal end of the balloon.

In a presently preferred embodiment, a soft tip member having at least a portion distal to the inner tubular member forms the distal end portion of the shaft, and defines a distal portion of the guidewire lumen in fluid communication with the portion of the guidewire lumen defined by the inner tubular member. The soft tip member provides improved flexibility at the shaft distal end for improved maneuverability. However, in an alternative embodiment, the soft tip member is omitted, and the distal end of the inner tubular member defines the distal end portion of the shaft. The soft tip member is typically softer and more flexible than the inner tubular member. In one embodiment, the soft tip member is formed of a material having a lower Shore Durometer hardness than a polymeric material forming at least part of the inner tubular member, to provide a soft, flexible, atraumatic distal end, which consequently provides improved catheter maneuverability and decreases the risk of damage to the patient's vessel during advancement of the catheter therein. The Shore Durometer hardness of the polymeric material forming the soft tip member is typically about 40D to about 70D, preferably about 55D to about 65D. In a presently preferred embodiment, the soft tip member is formed of a polyether block amide polymer such as PEBAX (available from Autochem). However, the soft tip member may be formed of a variety of suitable materials, including polyolefin based copolymers such as a polyethylene based adhesive polymer sold commercially as PRIMACOR (an ethylene-acrylic acid copolymer) by Dow Chemical Co., polyurethanes, and polyurethane copolymers such as PELLETHANE (a polyester polyurethane copolymer), available from Dow Plastics.

In a presently preferred embodiment, the outer sheath member is around a distal end of the inner tubular member and at least a proximal end of the soft tip member. However, a variety of suitable configurations may be used in which the location of the distal end of the shaft relative to the outer sheath varies. For example, in one embodiment, the distal end of the shaft is distal to the distal end of the outer sheath member, to provide an atraumatic leading distal end. However, in an alternative embodiment, the distal end of the outer sheath member is either aligned with or is distal to the distal end of the shaft, to provide enhanced support at the distal tip for improved tensile strength. In the embodiment having a soft tip member distal to the inner tubular member, the distal end of the inner tubular member is preferably located proximal to the sidewall break in the outer sheath, although it may alternatively be located distal to the proximal end of the sidewall break, depending on the desired performance characteristics of the catheter.

In a method of making a balloon catheter embodying features of the invention, the distal end portion of the catheter shaft is positioned in the lumen of the outer sheath member during assembly of the catheter. At least a portion of the outer sheath is heated and bonded to the distal end portion of the shaft, so that the polymeric material forming the outer surface of the shaft distal end portion at least partially fills the sidewall break in the outer sheath member to form the distal tip of the catheter. In a presently preferred embodiment, the outer sheath is heat fusion bonded to the distal end portion of the shaft, so that the bonding and the filling of the sidewall break is performed in the same step by heating the outer sheath and the shaft together. However, the outer sheath can additionally or alternatively be adhesively bonded to the shaft.

The catheter of the invention has excellent maneuverability and crossability due to the distal end of the catheter having a sidewall break filled with the polymeric material of the underlying section of the catheter shaft. The distal tip provides gradually increasing softness and flexibility at the catheter distal end and excellent strength at the distal tip attachment for improved handling and performance, without disadvantageously increasing the stiffness or profile of the distal end of the catheter. These and other advantages of the invention will become more apparent from the following detailed description and exemplary drawings.

DETAILED DESCRIPTION OF THE INVENTION

Figure 1:
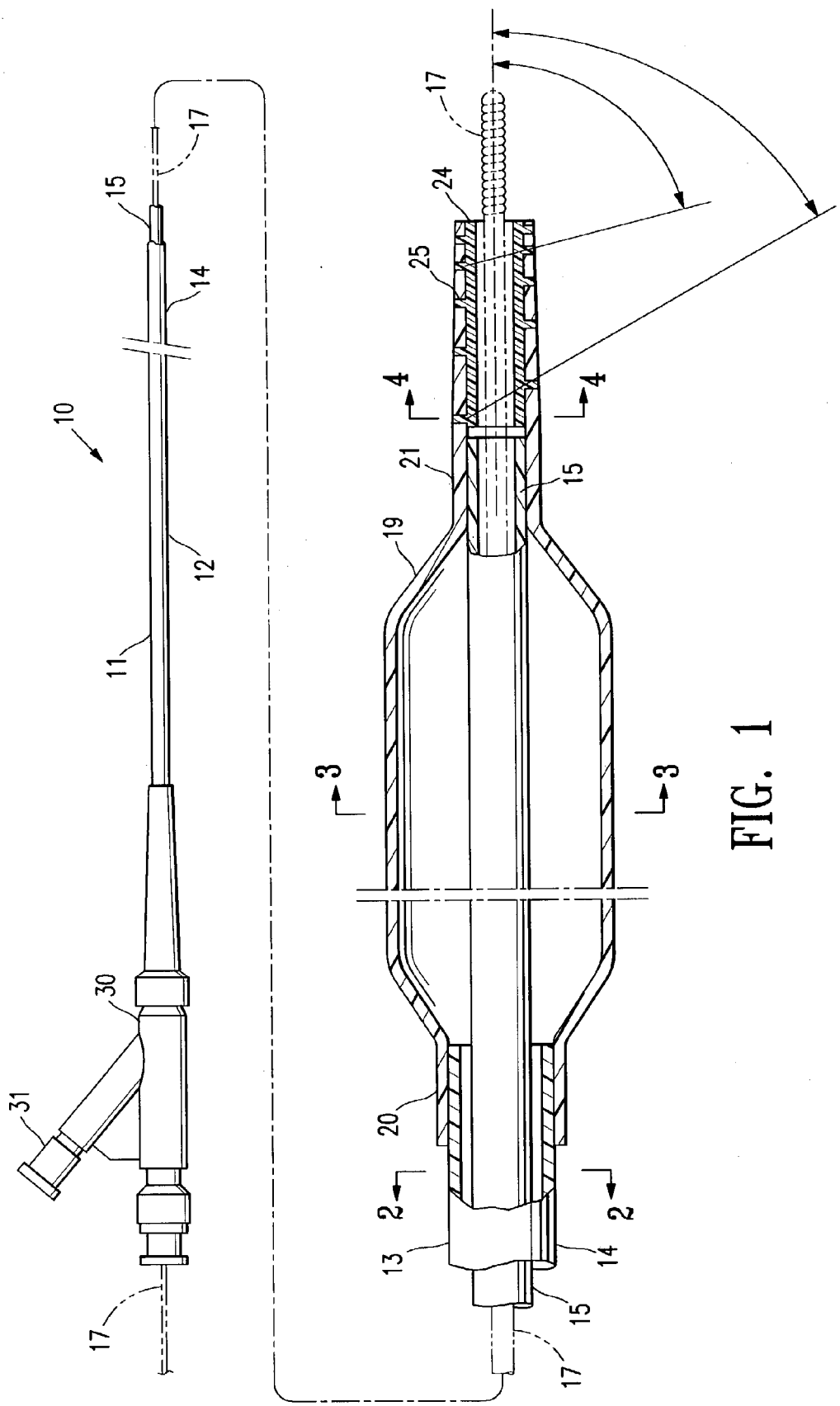
FIG. 1 is an elevational view, partially in section, of a balloon catheter which embodies features of the invention.
Figure 2:
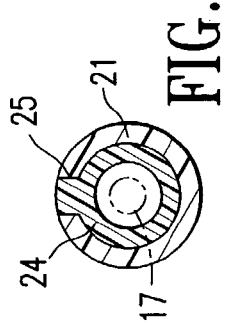
FIG. 2 is a transverse cross sectional view of the catheter shown in FIG. 1, taken along line 2—2.
Figure 3:
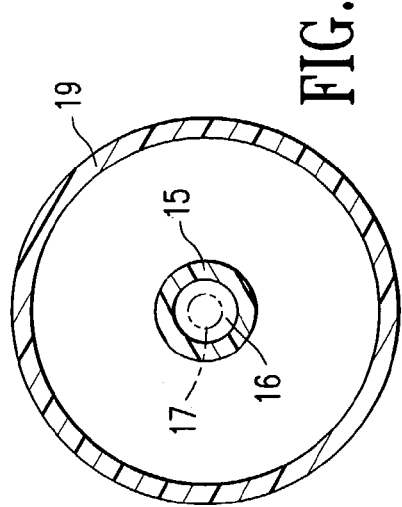
FIG. 3 is a transverse cross sectional view of the catheter shown in FIG. 1, taken along line 3—3.
Figure 4:
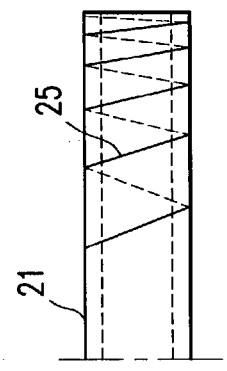
FIG. 4 is a transverse cross sectional view of the catheter shown in FIG. 1, taken along line 4—4.

FIG. 1 illustrates an over-the-wire balloon catheter 10 embodying features of the invention. Catheter 10 generally comprises an elongated catheter shaft 11 having proximal end, a distal end, a proximal shaft section 12, a distal shaft section 13, an outer tubular member 14, and an inner tubular member 15. Inner tubular member 15 defines a guidewire lumen 16 adapted to slidingly receive a guidewire 17 (shown in dashed lines in FIG. 1), and the coaxial relationship between outer tubular member 14 and inner tubular member 15 defines annular inflation lumen 18, as best shown in FIG. 2, illustrating a transverse cross section of the catheter of FIG. 1, taken along line 2—2. An inflatable balloon 19 is disposed on the distal shaft section 13, having a proximal skirt section 20 sealingly secured to the distal end of outer tubular member 14, and a distal skirt section 21 sealingly secured to the distal end of inner tubular member 15, so that its interior is in fluid communication with inflation lumen 18. In the embodiment of FIG. 1, the catheter 10 has a soft tip member 24 forming the distal end of the catheter shaft 11. The distal skirt section 21 is bonded, and preferably fusion bonded, to a distal end of the inner tubular member 15 and at least a proximal end of the soft tip member 24. The soft tip member 24 defines a distal portion of the guidewire lumen 16 in fluid communication with the proximal portion of the guidewire lumen 16 defined by the inner tubular member 15. An adapter 30 at the proximal end of the shaft is configured to provide access to guidewire lumen 16, and to direct inflation fluid through arm 31 into inflation lumen 18. FIG. 1 illustrates the balloon 19 inflated with a central working length section, and proximal and distal tapered sections between the working length and the proximal and distal skirt sections 20, 21, respectively. The distal end of catheter may be advanced to a desired region of a patient's body lumen in a conventional manner, and balloon 19 inflated to perform a procedure, and the balloon deflated, and the catheter repositioned or withdrawn from the body lumen. FIGS. 3 and 4 illustrate transverse cross sections of the catheter of FIG. 1, taken along lines 3—3, and 4—4, respectively.

The distal tip of the catheter 10, defining the distal end of the catheter 10, comprises an outer sheath member, which in the embodiment of FIG. 1 is formed by the distal skirt section 21 of balloon 19, fused to the soft tip member 24. Although illustrated with a circular transverse cross sectional shape in the figures, the distal skirt section 21 and underlying shaft section can have a variety of suitable shapes including oblong, and the like.

The distal skirt section 21 of balloon 19 has a sidewall break 25 spiraling longitudinally along a distal portion of the distal skirt section 21, and filled with the polymeric material of the soft tip member 24. The distal tip of the catheter 10 should be understood to refer to the portion of the catheter extending from the proximal end of the sidewall break 25 to the distal end of the catheter, to define the distal end of the catheter. In the embodiment of FIG. 1, the sidewall break 25 proximal end is located distal to the proximal end of the distal skirt section 21. The distal skirt section 21 thus has a proximal section which has a continuous wall around the circumference thereof. In the embodiment of FIG. 1, the distal end of the soft tip member 24 is radially aligned with the distal end of the distal skirt section 21, and the proximal end of the soft tip member 24 is proximal to the sidewall break 25. The distal end of the sidewall break 25 is preferably at or adjacent to the distal end of the distal skirt section 21 (i.e., the sidewall break 25 distal end is at the distal end of the distal skirt section 21 or is proximal to the distal end of the distal skirt section 21 by a distance which is no more than the width of the filled sidewall break 25). Preferably, the spiraling break 25 extends along a portion of the distal skirt section 21 which is about 50% to about 80% of the total length of the distal skirt section 21, and which, in one embodiment, is about 2.5 mm to about 4 mm.

The sidewall break 25 is completely filled with the polymeric material of the outer surface of the soft tip member 24. The outer surface of the soft tip polymeric material filling the sidewall break is in line with the outer surface of the distal skirt section 21. In alternative embodiments (not shown), the soft tip member 24 material only partially fills the sidewall break 25, so that the outer diameter of the soft tip material in the sidewall break is less than the outer diameter of the adjacent surface of the distal skirt section 21. The sidewall break spirals longitudinally at an angle relative to a longitudinal axis of the distal tip. In the illustrated embodiment, the angle increases toward the distal end of the distal tip, so that the angle of the distal-most spiral is more nearly perpendicular relative to the longitudinal axis than is the angle of the proximal-most spiral). In the embodiment of FIG. 1, the angle of the proximal-most spiral is about 60 degrees, and the angle of the distal-most spiral is about 76 degrees.

In the embodiment of FIG. 1, the soft tip member 24 has a proximal end spaced distally apart from the inner tubular member 15, forming a gap therebetween which is surrounded by the cylindrical proximal portion of the balloon distal skirt section 21. Although illustrated with a gap between the inner tubular member 15 and the distal tip member 24, a variety of suitable junctions between the distal tip member and the inner tubular member may be used including lap and butt joints.

Figure 5:
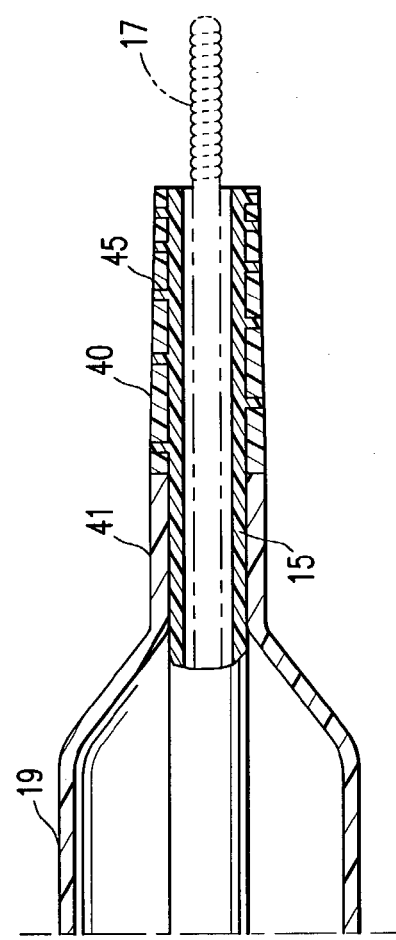
FIG. 5 is an enlarged, longitudinal cross sectional view of a distal end of an alternate embodiment of a catheter embodying features of the invention, having a sleeve member around the distal end of the shaft.

FIG. 5 illustrates a longitudinal cross section of an alternative embodiment, in which the outer sheath of balloon catheter 10 is an outer sleeve member 40 (instead of the balloon distal skirt section 21 of the embodiment of FIG. 1). In the embodiment of FIG. 5, the balloon 19 has a cylindrical distal skirt section 41 with a squared-off distal leading face abutting the proximal end of the outer sleeve member 40. Similar to the embodiment of FIG. 1, the outer sleeve member 40 has a sidewall spiraling break extending through a wall thereof. In the embodiment of FIG. 5, the soft tip member 24 of the embodiment of FIG. 1 is omitted, so that inner tubular member 15 forms the distal end of the shaft, and the polymeric material of the outer surface of the inner tubular member 15 is in the break 45 in the sidewall of the outer sleeve member 40. In the embodiment of FIG. 5, the distal end of the shaft 11 is distal to the distal end of the outer sleeve member 40, so that the distal end of the sidewall break 25 is spaced proximally apart from the distal end of the shaft.

The outer sleeve member 40 and balloon distal skirt section 41 are secured to the inner tubular member 15 as discussed above in relation to the embodiment of FIG. 1. Outer sleeve member 40 typically has a length of about 1 to about 4 mm. Although not illustrated, a distal tip member such as tip member 24 may be provided in the embodiment having an outer sleeve member 40, as for example with a tip member (not shown) butt-joined to the distal end of the inner tubular member 15 with outer sleeve member 40 sealingly surrounding the butt joint.

Figure 6:
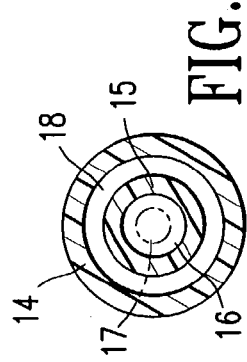
FIG. 6 is an enlarged, longitudinal cross sectional view of the distal skirt section of the balloon of FIG. 1, before bonding to the catheter shaft.

In a method of making a balloon catheter of the invention, the break 25, 45 is formed in the sidewall of the outer sheath member (i.e., the distal skirt section 21 or the outer sleeve member 40), preferably by mechanically cutting through the wall of the outer sheath member with a cutting blade. However, break 25, 45 may alternatively be formed by a variety of suitable methods including other methods of material removal such as laser cutting. Prior to being bonded to the catheter shaft, the outer sheath member is a tubular member with the break 25 in a wall thereof, and with a lumen therein configured to receive the catheter shaft therein so that the outer sheath member can be placed in surrounding relation to the shaft and subsequently bonded thereto. FIG. 6 illustrates the distal skirt section 21 with the spiraling break 25 in the wall thereof, before the catheter shaft 11 is positioned in the lumen of the distal skirt section 21 for bonding thereto. During bonding of the balloon distal skirt section 21 to the distal end of the shaft, the polymeric materials typically melt or soften, and flow. As a result, the polymeric material of the underlying portion of the shaft flows up into the break 25 in the wall of the distal skirt section 21, typically widening the width of the break 25. Specifically, in one embodiment of forming the catheter of FIG. 1, a mandrel is placed in the inner lumen of the shaft, and a heat shrink sleeve is provided on the outer surface of the distal skirt section 21 and heat is applied to a distal length thereof to bond the distal skirt section 21 to the underlying portion of the shaft. The polymeric materials typically flow distally as the members are forced down onto the mandrel, so that the resulting fusion bonded portion of the distal skirt section 21 has a tapered outer surface forming a distally decreasing wall thickness. In one embodiment, the fusion bonded portion of the distal skirt section 21 extends from a location distal of the proximal end of the distal skirt section 21 to the distal end of the distal skirt section 21, so that a proximal portion of the distal skirt section 21 is not bonded to the inner tubular member 15. The length of the bonded portion of the distal skirt section is typically about 60% to about 80% of the length of the balloon distal skirt section 21. Preferably, the distal skirt section 21 is trimmed or otherwise provided with a desired length before the fusion bonding, and thus the outer sheath member (distal skirt section 21 or outer sleeve member 40) lengthens during the bonding as the polymeric material of the underlying section of the shaft flows up into the sidewall break 25, 45. Alternatively, after the fusion bonding and cooling, the length of the distal skirt section 21 may be trimmed by cutting off the distal most end of the distal skirt section 21 to form the distal tip of the catheter.

To the extent not previously discussed herein, the various catheter components may be formed and joined by conventional materials and methods. For example, inner tubular member 15 can be formed by conventional techniques, such as by extruding and necking materials found useful in intravascular catheters such a polyethylene, polyvinyl chloride, polyesters, polyamides, polyimides, polyurethanes, and composite materials, and is preferably a multilayered tubular member. Additionally, although not illustrated, coiled or braided reinforcements may be included in the shaft at various locations, as is conventionally known. In one embodiment, the polymeric material of the outer sheath member (i.e., the distal skirt section 21 or the outer sleeve member 40) is preferably compatible with the polymeric material of the underlying section of the shaft (i.e., the soft tip member 24 or the inner tubular member 15), to facilitate fusion bonding thereto.

The length of the dilatation catheter 10 is generally about 108 to about 200 centimeters, preferably about 137 to about 143 centimeters, and typically about 143 centimeters for PTCA. The outer tubular member 14 distal section has an outer diameter (OD) of about 0.028 to about 0.036 inch (0.70–0.91 mm), and an inner diameter (ID) of about 0.024 to about 0.035 inch (0.60–0.89 mm), and the outer tubular member 14 proximal section has an OD of about 0.036 to about 0.042 inch (0.9–1 mm), and an inner diameter (ID) of about 0.034 to about 0.036 inch (0.86–0.9 mm). The inner tubular member 15 has an OD of about 0.017 to about 0.026 inch (0.43–0.66 mm), and an ID of about 0.015 to about 0.02 inch (0.38–0.5 mm), depending on the diameter of the guidewire to be used with the catheter. The balloon 19 has a length of about 8 mm to about 40 mm, and an inflated working diameter of about 1.5 mm to about 5 mm.

While the present invention has been described herein in terms of certain preferred embodiments, those skilled in the art will recognize that modifications and improvements may be made without departing from the scope of the invention. For example, although the catheter 10 illustrated in the Figures is an over-the-wire balloon catheter, the catheter of the invention may be a variety of suitable balloon catheters, including rapid exchange type balloon catheters having a guidewire proximal port located distal to the proximal end of the shaft, a guidewire distal port in the distal end of the shaft, and a relatively short guidewire lumen extending therebetween. While individual features of one embodiment of the invention may be discussed or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated shaft having a proximal end, a distal end, and at least one lumen;
   b) a balloon on a distal shaft section, having an inflatable interior in fluid communication with the at least one lumen of the shaft; and
   c) a distal tip defining the distal end of the catheter, having at least a section formed by a distal end portion of the shaft and an outer sheath member bonded together, the outer sheath member comprising a first polymeric material having a higher Shore durometer hardness than a second polymeric material forming an outer surface of the shaft distal end portion, the outer sheath member having a sidewall break at least partially filled with the polymeric material of the outer surface of the distal end portion of the shaft, wherein the sidewall break of the outer sheath member spirals longitudinally at an angle relative to a longitudinal axis of the distal tip.

2. The catheter of claim 1 wherein the balloon has a proximal skirt section and a distal skirt section sealingly securing the balloon to the shaft, and the outer sheath member of the distal tip is formed by at least a portion of the distal skirt section of the balloon.

3. The catheter of claim 2 wherein polymeric material of the distal end portion of the shaft completely fills the sidewall break of the distal skirt section, so that the distal end portion of the shaft has an outer surface with a first part fusion bonded to an inner surface of the balloon distal skirt section, and with a second part extending in the spiraling sidewall break of the distal skirt section and having an outer surface longitudinally aligned with an outer surface of the balloon distal skirt section.

4. The catheter of claim 2 wherein the shaft further comprises a soft tip member and the balloon distal skirt section sealingly surrounds the distal end of the inner tubular member and at least the proximal end of the soft tip member.

5. The catheter of claim 2 wherein the spiraling break extends along a portion of the balloon distal skirt section which is about 50% to about 80% of the total length of the balloon distal skirt section.

6. The catheter of claim 1 wherein the outer sheath member of the distal tip is a sleeve member having at least a portion distal to the balloon.

7. The catheter of claim 1 wherein the angle of the spiraling sidewall break varies along a length of the distal tip.

8. The catheter of claim 1 wherein the angle of the spiraling sidewall break increases towards a distal end of the distal tip.

9. The catheter of claim 8 wherein the angle of the spiraling sidewall break is about 30 to about 60 degrees at a proximal end of the distal tip and increases towards the distal end of the distal tip to about 45 to about 85 degrees.

10. The catheter of claim 1 wherein the spiraling sidewall break extends distally to a location adjacent to the distal end of the distal tip.

11. The catheter of claim 1 wherein the spiraling sidewall break extends distally to a location proximally spaced apart from the distal end of the distal tip.

12. The catheter of claim 1 wherein the at least one lumen of the shaft is an inflation lumen, and the shaft comprises an outer tubular member defining the inflation lumen, and an inner tubular member defining at least a portion of a guidewire receiving lumen.

13. The catheter of claim 12 wherein the shaft further comprises a soft tip member, and the distal end portion of the shaft is formed by the soft tip member, the soft tip member having at least a portion distal to the inner tubular member, and defining a distal portion of the guidewire lumen in fluid communication with the portion of the guidewire lumen defined by the inner tubular member.

14. The catheter of claim 12 wherein the distal end portion of the shaft is formed by the inner tubular member.

15. A balloon catheter, comprising:
a) an elongated shaft having a proximal end, a distal end, and at least one lumen;
b) a balloon on a distal shaft section, having an inflatable interior in fluid communication with the at least one lumen of the shaft; and
c) a distal tip defining the distal end of the catheter, having at least a section formed by a distal end portion of the shaft and an outer sheath member bonded together, the outer sheath member comprising a first polymeric material, a second polymeric material forming an outer surface of the shaft distal end portion, the outer sheath member having a sidewall break at least partially filled with the polymeric material of the outer surface of the distal end portion of the shaft, wherein the sidewall break of the outer sheath member spirals longitudinally at an angle relative to a longitudinal axis of the distal tip.

* * * * *